United States Patent [19]
della Valle et al.

[11] Patent Number: 5,925,626
[45] Date of Patent: *Jul. 20, 1999

[54] HYALURONIC ACID FRACTIONS HAVING PHARMACEUTICAL ACTIVITY, AND PHARMACEUTICAL COMPOSITIONS CONTAINING THE SAME

[75] Inventors: Francesco della Valle, Padua; Aurelio Romeo, Rome, both of Italy

[73] Assignee: Fidia S.p.A., Abano Terme, Italy

[*] Notice: This patent is subject to a terminal disclaimer.

[21] Appl. No.: 08/471,016

[22] Filed: Jun. 6, 1995

Related U.S. Application Data

[63] Continuation of application No. 07/725,765, Jun. 28, 1991, which is a continuation of application No. 07/494,423, Mar. 16, 1990, abandoned, which is a continuation of application No. 06/719,113, Apr. 2, 1985, abandoned, which is a continuation of application No. 06/564,906, Dec. 23, 1984, abandoned.

[30] Foreign Application Priority Data

Oct. 10, 1983 [IT] Italy ........................ 49143/83

[51] Int. Cl.⁶ .............................. A61K 31/70; C07H 5/04
[52] U.S. Cl. ............................ 514/54; 536/54; 536/55.1; 536/55.2
[58] Field of Search .................. 536/55.2, 55.3, 536/55.1, 54; 514/54, 514

[56] References Cited

U.S. PATENT DOCUMENTS

| | | | |
|---|---|---|---|
| 4,141,973 | 2/1979 | Balazs | 514/54 |
| 4,272,522 | 6/1981 | Balazs | 424/94.61 |
| 4,303,676 | 12/1981 | Balazs | 514/773 |
| 4,328,803 | 5/1982 | Pape | 514/54 |
| 4,517,295 | 5/1985 | Bracke et al. | 435/101 |

OTHER PUBLICATIONS

Laurent et al., Chemical Abstracts, 98:211815f (1983).
Cleland, Chemical Abstracts, 76:43075q (1972).
Shimada et al, J. Biochem., 81, pp. 79–91 (1977).
Barron et al., American Journal of Ophthalmology, 100, pp. 377–384 (1985).
Richter et al., Int. Archs. Allergy appl. Immun. 59, pp. 45–48 (1979).
Balazs et al., Ciba Foundation Symposium 143, The Biology of Hyaluronan, ed. John Wiley & Sons, pp. 265–267 (1989).
Stegmann et al., Annals of Ophthalmology, pp. 813–815 (1982).
Cherfan et al., Trans., Opthal. S. K., 103, pp. 277–278 (1983).
MacRae et al., American Journal of Ophthalmology, 95, pp. 332–341 (1983).
Lane et al., J. Cataract Refract Surg., 17, pp. 21–26 (1991).
Alpar et al., Ophthalmic Surgery, 19, pp. 636–642 (1988).
Fry, J. Cataract Refract. Surg., 15, pp. 415–420 (1989).
Abatangelo et al., Exp. Cell Research, 137, pp. 73–78 (1982).
Swann, Biochim, Biophys. Acta, 156, pp. 17–30 (1968).

*Primary Examiner*—Elli Peselev
*Attorney, Agent, or Firm*—Birch, Stewart, Kolasch & Birch, LLP

[57] ABSTRACT

Two pharmaceutically useful fractions of hyaluronic acid are obtained comprising a first fraction with a molecular weight between 50,000 and 100,000 which is useful for wound healing, and a second fraction having a molecular weight between 500,000 and 730,000 which is useful for intraocular and intraarticular injections.

22 Claims, 1 Drawing Sheet

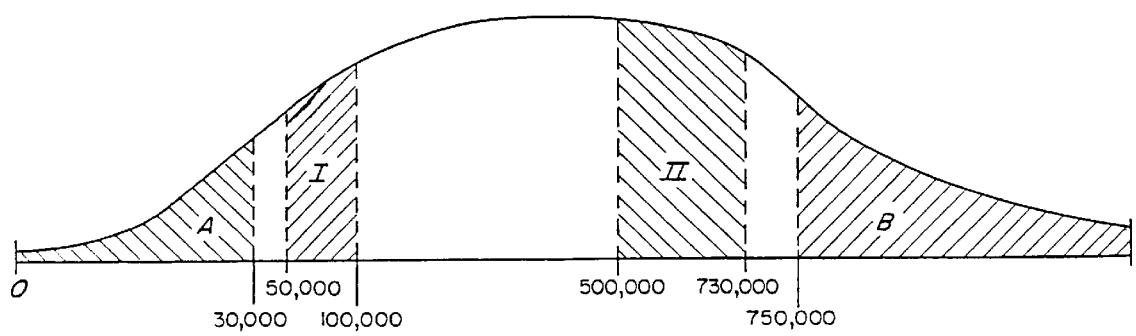
AVERAGE MOLECULAR WEIGHT OF HYALURONIC ACID

HYALURONIC ACID FRACTIONS HAVING PHARMACEUTICAL ACTIVITY, AND PHARMACEUTICAL COMPOSITIONS CONTAINING THE SAME

This application is a continuation of application Ser. No. 07/725,765, filed on Jun. 28, 1991, which is a continuation of Ser. No. 07/494,423 filed Mar. 16, 1990, now abandoned, which is a continuation of Ser. No. 719,113 filed Apr. 2, 1985, now abandoned, which is a continuation of Ser. No. 564,906 filed Dec. 23, 1984, now abandoned, the entire contents of which are hereby incorporated by reference.

BACKGROUND AND FIELD OF THE INVENTION

This invention relates to specific molecular weight fractions of hyaluronic acid (hereinafter referred to as "HA") which have therapeutic applications and which are non-inflammatory when utilized. One of the HA fractions of this invention is useful for facilitating wound healing, while the second HA fraction is useful for intraocular use to substitute for endobulbar fluids or for intraarticular injection for use in treating damaged bone joints.

Hyaluronic acid is a naturally occurring heteropolysaccharide consisting of alternating residues of D-glucuronic acid and N-acetyl-D-glucosamine. HA is a linear polymer of high molecular weight, generally up to about 8 to 13 million, and has been found in cell coats, the extracellular ground substance of connective tissues of vertebrates, in the synovial fluid in joints, in the endobulbar fluids of the eye, in human umbilical cord tissue, and in rooster combs.

Previous investigations on the use of HA are included in the work of Balazs, U.S. Pat. No. 4,141,973, directed to a fraction of HA useful for replacing endobulbar fluids, as well as other therapeutic applications. This patent, however, is specifically directed to an HA fraction having an average molecular weight greater than about 750,000, and preferably greater than about 1,200,000. Balazs specifically teaches that fractions of HA having an average molecular weight of less than 750,000 are not therapeutically useful because of their inflammatory activity. These lower molecular weight fractions of HA are discarded by Balazs. However, this results in discarding about 90% of the total amount of available HA obtainable from the source tissues, resulting in a use of only a small amount (about 10%) of the available HA.

Contrary to the teachings of Balazs, the present inventors have discovered that lower molecular weight fractions of HA do indeed have useful pharmaceutical activity. Thus, according to the present invention, about 80% of the HA obtainable from various sources is utilized. In particular, the present inventors have discovered one fraction of HA which is useful for stimulating wound healing, and a second fraction of HA which is useful for intraocular injections to substitute for the endobulbar liquids in the eye and for intraarticular injections as a treatment for damaged joints.

OBJECTS AND SUMMARY OF THE INVENTION

It is, therefore, one object of the present invention to provide specific well defined fractions of hyaluronic acid having pharmaceutical applications and without inflammatory activity.

It is another object of the present invention to provide a fraction of HA which is useful for stimulating wound healing.

It is another object of the invention to provide a fraction of HA which is useful for intraocular and intraarticular injections for replacing the endobulbar liquids in the eye and for treating damaged bone joints, respectively.

It is a further object of the present invention to provide fractions of HA which are therapeutically useful and which permit the use of a high percentage of the available HA that can be obtained from source tissues.

It is still a further object of the present invention to provide a method for obtaining specific fractions of HA depending upon the average molecular weight for differing therapeutic applications.

These and other objects of the present invention are accomplished by obtaining two specific well defined fractions of hyaluronic acid. According to the invention, one fraction of HA having an average molecular weight of between about 50,000 to about 100,000 is useful for wound healing, and a second fraction of HA having an average molecular weight of about 500,000 to about 730,000 is useful for intraocular and intraarticular injections.

BRIEF DESCRIPTION OF THE DRAWING

The attached FIGURE is a graph showing the different fractions of hyaluronic acid which have been identified by the present inventors.

DETAILED DESCRIPTION OF THE INVENTION

As discussed above, previous investigations of HA, as exemplified by the Balazs patent, have been directed to utilizing high molecular weight fractions with an average molecular weight of greater than 750,000. The present inventors have isolated and characterized two new fractions of HA, one having a low molecular weight and another having a medium ranged average molecular weight, which are of a high degree of purity and do not have inflammatory activity. These new fractions of HA can be obtained from various connective tissues which contain extractable amounts of hyaluronic acid. The specific fractions of the invention are differentiated and separated according to molecular filtration techniques.

The first fraction isolated by the inventors has been named HYALASTINE, and has an average molecular weight of from about 50,000 to about 100,000. This HYALASTINE fraction has been determined to be suitable for therapeutic, veterinary and human use because of its wound healing activity. The second fraction isolated by the inventors has been labeled HYALECTIN, and has an average molecular weight of about 500,000 to about 730,000. This HYALECTIN fraction is suitable for use in ocular surgery as a substitute for endobulbar liquids and for veterinary and human therapy in traumatic and degenerative diseases of the joints.

HYALASTINE can be administered either as an intradermal injection or it can be applied as a topical agent for wound healing. HYALECTIN, on the other hand, is suitable for intraocular and intraarticular injection.

The present inventors have made intensive studies on the various fractions of HA and, in a significantly more precise way than previously accomplished, have specifically determined the therapeutically useful fractions of HA and the inflammatory and non-useful fractions of HA. As a result of these studies, the present inventors have identified and investigated two specific characteristics of HA fractions, namely cell mobilization activity and intrinsic viscosity. The wound healing process in animals is facilitated by cellular mobilization, and particularly the mobilization of fibroblasts. On the other hand, cellular mobilization or proliferation activity (i.e., mytosis) is to be avoided in cases of surgery inside the ocular globe. This is particularly true in operations to correct retinal detachment where an increased rate of healing may cause harmful affects.

The intrinsic viscosity is also an important parameter to be considered in determining the utility of a fraction of HA. A fraction having a high intrinsic viscosity is useful for surgical uses, in the therapy of diseases of the joints of a traumatic and degenerative nature, and for replacing endobulbar liquids. On the other hand, high viscosity is an undesirable characteristic for fractions to be utilized as drugs for facilitating wound healing. In fact, fractions to be utilized in wound healing should have low viscosity so as to be more easily used in practical application.

The HYALASTINE fraction identified by the present inventors has been determined to have good mobilization or cell proliferation activity, and low viscosity characteristics. Accordingly, HYALASTINE has the characteristics desirable for a material useful in promoting wound healing. The same characteristics make the HYALASTINE fraction undesirable for use in intraocular or intraarticular injection treatments.

The HYALECTIN fraction identified by the inventors has been determined to have negligible cell mobilization or proliferation activity, while at the same time having high viscosity. These characteristics, therefore, make the HYALECTIN fraction useful for intraocular and intraarticular injection treatments. But, on the other hand, HYALECTIN is not useful for wound healing treatments since this fraction does not exhibit cell mobilization activity.

In isolating useful fractions of hyaluronic acid, it is also important to obtain those fractions which do not have inflammatory activity. The Balazs patent noted above teaches that in order to obtain hyaluronic acid fractions without inflammatory activity, fractions having an average molecular weight of more than 750,000 must be utilized exclusively. Thus, Balazs discards the fractions having less than 750,000 average molecular weight as being non-useful because of inflammatory activity. Contrary to the teachings of Balazs, the present inventors have found that the inflammatory activity attributed by Balazs to fractions having an average molecular weight of less than 750,000 is actually due to impurities having an average molecular weight of less than 30,000. Thus, the present invention provides a method which comprises a series of molecular filtration techniques associated with chemical methods by which the inflammatory fraction having a molecular weight of less than 30,000 can be eliminated.

By the methods of the invention, it is possible to obtain useful fractions of hyaluronic acid having no inflammatory activity which, when considered together, constitute a total yield of about 80% of the total hyaluronic acid available from the particular starting materials. This 80% yield of the available hyaluronic acid comprises a combined fraction which is a combination of the HYALECTIN and HYALASTINE fractions and which has an average molecular weight of from about 250,000 to about 350,000. More specifically, the HYALECTIN fraction is obtained in a yield of about 30% of the available HA and the HYALASTINE fraction is obtained in a yield of about 50% of the available HA from the starting tissues. This factor is an important improvement over the process of the Balazs patent discussed above in that the present inventors have discovered that significantly increased amounts of the available hyaluronic acid are pharmaceutically useful. By utilizing only the fraction having an average molecular weight of greater than 750,000, the Balazs process obtains a yield of only about 10% of the original hyaluronic acid available from animal organs, and discards about 90% of the available hyaluronic acid. Thus, according to the present invention, the usefulness of the total hyaluronic extract has been greatly increased.

A comparison of the relative yields of the extraction of various fractions of hyaluronic acid is presented below in Table 1.

TABLE 1

| Type of Hyaluronic Acid | g per 100 g of fresh tissue | % | Reference |
| --- | --- | --- | --- |
| Total hyaluronic acid from rooster combs | 0.8 | 100 | Swann D.A. 1968, Biochim, Biophys. Acta 156, 17–29 |
| HA (Balazs type) | 0.08 | 10 | U.S. Pat. No. 4,141,973 |
| HYALECTIN + HYALASTINE | 0.6 | 80 | present invention |
| HYALECTIN | 0.2 | 30 | present invention |
| HYALASTINE | 0.4 | 50 | present invention |
| Inflammatory fraction | 0.16 | 20 | present invention |

FIG. 1 graphically shows the different HA fractions which the present inventors have identified. The solid bell-shaped curve of FIG. 1 represents the approximate distribution of the HA fractions available from a starting tissue. Area "B" in FIG. 1 represents the HA fraction identified by Balazs in U.S. Pat. No. 4,141,973 as being pharmaceutically useful. Areas "A", I and II in FIG. 1 are the fractions identified by the present inventors—area A being the inflammatory fraction having an average molecular weight less than 30,000; area I being the HYALASTINE fraction; and area II being the HYALECTIN fraction. From this graph, it can be seen that the Balazs method discards the large majority of available extractable HA by eliminating the HA fractions having an average molecular weight of less than 750,000. The present invention, on the other hand, permits the pharmaceutical use of a large proportion of available HA since the low molecular weight hyaluronic acid fraction having an average molecular weight of less than 30,000 causes the inflammatory activity which previous investigators have noted with various extracts of HA.

The present inventors have discovered that a large percentage of available HA can, in fact, be utilized for therapeutic purposes if separated according to the teachings of this invention depending upon the particular therapeutic application. While the Balazs patent specifically teaches the use of only about 10% of the available HA, the present invention permits the use of about 80% of the available HA either in the form of the HYALASTINE fraction for wound healing applications, or in the form of the HYALECTIN fraction for intraocular and intraarticular applications, or in the form of a combined HYALASTINE and HYALECTIN fraction which can also be used for wound healing applications.

The chemical and physical characteristics of the identified fractions have also been investigated by the present inventors, and these characteristics are summarized in Table 2.

METHODS OF PREPARATION

EXAMPLE 1

Method for Obtaining a Mixture of HYALASTINE and HYALECTIN Fractions without Inflammatory Activity;

Hen crests, either fresh or frozen (3000 g), are minced in a meat mincer and then carefully homogenized in a mechanical homogenizer. The resulting paste is placed in an AISI 316 stainless steel container or in a glass container with 10 volumes of anhydrous acetone.

TABLE 2

CHEMICAL AND PHYSICAL CHARACTERISTICS

| Fractions | M.W. | Dynamic viscosity at 20% C | Titer in hyaluronic acid of % dry powder | Content in proteins as bovine albumin | Content in sulphurated mucopolysac-charides |
|---|---|---|---|---|---|
| HYALASTINE + HYALECTIN | 250,000–350,000 | 100 mP.s. (conc. 1% w/v) | >96%[a] | <0.5% | <1% |
| HYALASTINE | 50,000–100,000 | 600 mP.s. (conc. 5% w/v) | >96% | <0.5% | <1% |
| HYALECTIN | 500,000–730,000 | 170 mP.s. (conc. 1% w/v) | >96% | <0.5% | <1% |

[a]Values presented represent the titer in HA after elimination in water. For example, a titer of 96% represents that, after elimination of water, the powder contains 4% impurities and 96% hyaluronic acid.

The entire content is then agitated for 6 hours at a speed of 50 g/minute and left to separate for 12 hours, after which the acetone is syphoned off and discarded.

This extraction process is repeated until the discarded acetone has reached the correct humidity level (Karl-Fischer method).

The resulting substance is then centrifuged and vacuum dried at a suitable temperature for 5–8 hours. With this process, approximately 500–600 g of dry powder is obtained from the hen crests.

300 g of the dry powder is then submitted to an enzymatic digestion process with papain (0.2 g) through a buffered aqueous medium with a phosphate buffer in the presence of a suitable quantity of cysteine hydrochloride. This mixture is then agitated for 24 hours at 60 g/minute at a constant temperature of 60–65° C. This whole mass is cooled to 25° C. adding 60 g of Celite® and the agitation is maintained for an additional hour.

The resulting mixture is filtered until a clear liquid is obtained. This clear liquid then undergoes molecular ultrafiltration by means of membranes with a molecular exclusion limit of 30,000 to retain on the membrane those molecules with a molecular weight of greater than 30,000. Five to six original volumes are ultrafiltered and, at the same time, distilled water is continually added to the product. The addition of distilled water is suspended and the product is ultrafiltered until it is reduced to one-third of its original volume.

The residue liquid is rendered 0.1M by adding sodium chloride and the temperature is brought to 50° C. 45 g of cetylpyridinium chloride is added while the product is being agitated at 60 g/minute. This mixture is agitated for 60 minutes, after which 50 g of Celite® is added. Under agitation the temperature of the product is reduced to 25° C. and the precipitate formed is collected by means of centrifugation. The precipitate thus obtained is suspended in a 0.01M solution of sodium chloride (5 liters) containing 0.05% cetylpyridinium chloride. It is agitated for a further 60 minutes at 50° C. The temperature is lowered to 25° C. and the precipitate centrifuged.

The washing process is then repeated three times and the precipitate finally gathered into containers holding 3 liters of a 0.05M solution of sodium chloride containing 0.05% of cetylpyridinium chloride. This is agitated at 60 g/minute for 60 minutes and maintained at a constant temperature of 25° C. for a period of 2 hours. The lipid supernatant is eliminated by means of centrifugation.

The procedure is thus repeated several times with a 0.1M sodium chloride solution containing 0.05% of cetylpyridinium chloride. The mixture is centrifuged and the supernatant discarded. The precipitate is dispersed in a 0.30M sodium chloride solution containing 0.05% of cetylpyridinium chloride (3 l). The mixture is agitated and both the precipitate and the clear liquid are gathered. Extraction is repeated on the precipitate an additional 3 times, each time using 0.5 liters of the same aqueous solution.

Finally, the residue precipitate is eliminated and the clear liquids united in a single container. The temperature of the liquid is increased to 50° C. while agitating. The liquid is then brought to 0.23M with sodium chloride. 1 g of cetylpyridinium chloride is added and agitation maintained for 12 hours. The mixture is cooled to 25° C. then filtered, first through Celite® packs and then through a filter (1 µ).

The resultant mixture then undergoes a further molecular ultrafiltration through membranes with a molecular exclusion limit of 30,000, ultrafiltering 3 original volumes with the addition of a 0.33M sodium chloride solution. The addition of the sodium chloride solution is suspended and the volume of the liquid reduced to a quarter of its original volume.

The solution thus concentrated is precipitated under agitation (60 g/minute) at a temperature of 25° C. with three volumes of ethanol (95%). The precipitate is collected by centrifugation and the supernatant discarded. The precipitate is dissolved in 1 liter of 0.1M sodium chloride solution and the precipitation procedure is repeated with three volumes of 95% ethanol.

The precipitate is gathered and washed, first with 75% ethanol (three times), then with absolute ethanol (three times) and thirdly with absolute acetone (three times).

The product thus obtained (HYALASTINE+HYALECTIN fraction) has an average molecular weight between 250,000 and 350,000.

The hyaluronic acid yield is equal to 0.6% of the original fresh tissue.

EXAMPLE 2

Method for Obtaining the HYALASTINE Fraction from the Mixture Obtained by the Method Described in Example 1

The mixture obtained by the method described in Example 1 is dissolved in pyrogen free distilled water in proportions of 10 mg of product in 1 ml of water. The solution thus obtained undergoes molecular ultrafiltration through membranes with a molecular exclusion limit of 200,000 with a concentration technique and without addition of water on the membrane. During the ultrafiltration process through membranes with an exclusion limit of 200,000, molecules with molecular weight greater than 200,000 will not pass, whereas smaller molecules will pass through the membrane along with the water. During the filtration process no water is added in the compartment above the membrane; therefore, the volume in this compartment will decrease, along with an increase in the concentration of molecules with M.W. over 200,000. It is then ultrafiltered until the volume on the membrane is reduced to 10% of the initial volume. Two volumes of pyrogen free bidistilled water are added and the solution is again ultrafiltered until the volume is reduced to one-third. The operation is repeated another two times.

The solution which passes through the membrane is brought to 1.0M with sodium chloride and then precipitated with four volumes of ethanol at 95%. The precipitate is washed three times with 75% ethanol and then vacuum dried.

The product thus obtained (HYALASTINE fraction) has an average molecular weight between 50,000 and 100,000.

The hyaluronic acid yield is equal to 0.40% of the original fresh tissue.

EXAMPLE 3

Method of Obtaining HYALECTIN Fraction

The concentrated solution, gathered into a container from the ultrafiltration membrane with a molecular exclusion limit of 200,000 described in Example 2, is diluted with water until a solution containing 5 mg/ml of hyaluronic acid is obtained, as determined by quantitative analysis based upon an assay of glucuronic acid.

The solution is brought to 0.1M in sodium chloride and then precipitated with 4 volumes of 95% ethanol. The precipitate is washed three times with 75% ethanol and then vacuum dried.

The product thus obtained (HYALECTIN fraction) has an average molecular weight between 500,000 and 730,000. This corresponds to a specific hyaluronic acid fraction of defined molecular chain length of about 2,500 to 3,500 saccharide units with a high degree of purity.

The hyaluronic acid yield is equal to 0.2% of the original fresh tissue.

EVALUATION OF BIOLOGICAL AND PHARMACEUTICAL ACTIVITY

L. Biological Activity of Cellular Mobilization of the Hyaluronic Acid Fractions The method, consisting of the determination of the detachment activity of fibroblasts in culture, was used as the method for evaluating the cell mobilization activity of the HA fractions.

Mouse BALB 3T3 cells were grown in Dulbecco's modified Eagle medium supplemented with 10% calf serum, penicillin (250 units/ml) and streptomycin (0.25 mg/ml), and were incubated in humidified 5% $CO_2$, 95% air at 37° C. For experimental purposes, cells were routinely inoculated in 60-mm diameter plastic tissue culture dishes ($6 \times 10^5$ cells/dish).

Confluent monolayers of 3T3 cells were decanted and fresh medium containing 2.0 mg/ml of different fractions of HA were added. At fixed intervals, the cell detachment was observed both microscopically and by counting the mobilized cells in a Coulter Counter.

Detachment assay: To measure detachment kinetics, cells were inoculated into plastic dishes and allowed to grow for 24 hours. After this time, the culture medium was decanted and fresh medium containing 2.0 mg/ml of HA was added. Every 24 hours, two dishes, one each of test culture and of control culture, were decanted and both the cells in the supernatant and the attached cells were counted in a Coulter Counter.

Table 3 reports the results obtained with tests using the fractions obtained in the preparation Examples 1–3 above.

TABLE 3

RESULTS OP MOBILIZATION STUDIES

| Fraction | Concentration (mg/ml) | No. of Detached Cells as Compared to Controls | % Effectiveness (as compared to control) |
|---|---|---|---|
| Control | | $2 \times 10^6$ | |
| HYALECTIN + HYALASTINE | 2 | $3.5 \times 10^6$ | 75 |
| HYALECTIN | 2 | $2.1 \times 10^6$ | 5 |
| HYALASTINE | 2 | $5 \times 10^6$ | 150 |

The data reported in Table 3 shows that the HYALASTINE fraction exhibits high cell mobilization activity making this fraction useful for wound healing applications. This cell mobilization activity of HYALASTINE will stimulate migration and proliferation of new cells when a pharmaceutical preparation of the fraction is applied to a damaged tissue area.

The HYALECTIN fraction, on the other hand, exhibits very little cell mobilization activity and would not, therefore, be useful for wound healing. HYALECTIN, however, because of its high average molecular weight and inherent viscosity, is useful for ocular and intraarticular injections, and the lack of appreciable cell mobilization activity is an important characteristic of the HYALECTIN fraction making it especially useful for intraocular and intraarticular injections.

2. Biological Inflammatory Activity of the Hyaluronic Acid Fractions:

For this evaluation, the method of invasive cell count after intraocular administration in rabbits is utilized.

Method

Five (5) New Zealand or California rabbits, weighing about 2 kg and with ascertained perfect vision, are used for this test. The outer eye of the rabbits is checked for inflammatory processes at a macroscopic level and the inner eye is checked by ophthalmoscope. If the ocular fundus is clearly visible and normal, the test may proceed.

The selected animals undergo local anaesthetic by the instillation of a few drops of a suitable sterile anaesthetic for ophthalmology; a few drops of atropine in ophthalmological solution are also instilled.

The test is carried out in sterile conditions. The ocular globe is made to protrude by means of pressure until it is possible to inject, through the sclera at about 5–6 mm from the limbus, at the center of the vitreal cavity, 100 µl of the solution, using a 26 G needle. The other eye is taken as a control. Two drops of antibiotic solution are instilled in the treated eye and the animals are then housed in single cages.

After 50–60 hours the test may proceed further. The eyes are checked in the same way as above for the selection of the animals. The animals are sacrificed with an intravenous injection of Pentothal. Then, firstly, the aqueous humor (about 0.2 ml) is gathered by means of an insulin syringe with a 26 G needle. The ocular globes are then enucleated, freed from all foreign matter, washed in saline, dried with bibulous paper, and incised and opened in Petri plates, separating the main part of the vitreous humor and gathering it with a sterile syringe (about 0.7 ml). The vitreous humor is placed in small polyethylene test tubes and 50 µl of hyaluronidasc (100 U NF/ml) is added, The mixture is then kept at a temperature of 37° C. for about 3 hours in order to render the solution less viscous.

A leukocyte count is carried out under a microscope by phase contrast (120×) in a Burker chamber. A series of counts is effected on each sample, calculating the average values and expressing the result as the number of leukocytes per $mm^3$.

The test is considered positive when:

1) the eyes examined show no signs of suffering, and
2) the average number of leukocytes from at least 4 of the 5 treated eyes does not exceed 200 per $mm^3$ and the average number of leukocytes from each control eye does not exceed 50 per $mm^3$.

Table 4 reports the results obtained from this evaluation using the HA fractions obtained in preparation Examples 1–3 discussed above.

TABLE 4

RESULTS OF INFLAMMATORY ACTIVITY STUDIES

| Fraction | No. of Invasive Cells |
| --- | --- |
| Control | 25 |
| HYALASTINE + HYALECTIN | 32 |
| HYALASTINE | 20 |
| HYALECTIN | 22 |
| Inflammatory Fraction (Avg. MW of <30,000) | 150 |
| Total Hyaluronic Acid from Rooster Combs (RF. Swann D.A. 1968, B.B.A. 156, 17–29) | 120 |

The results reported in Table 4 show that the HYALASTINE and HYALECTIN fractions exhibit no inflammatory activity above that for the control, and the combined HYALASTINE and HYALECTIN fraction showed only a negligible increase in inflammatory activity over the control. Accordingly, the HYALASTINE and HYALECTIN fractions are pharmaceutically useful without exhibiting undesirable inflammatory side effects. These results also further confirm the inventors discovery that it is the HA fraction having a low average molecular weight of less than about 30,000 which is responsible for the inflammatory activity of HA preparations. Hyaluronic acid from rooster combs, prepared according to the method described in the literature by Swann (Swann D. A. 1968, B.B.A, 156, 17–29), shows a remarkable inflammatory activity.

It has thus been shown that the HYALASTINE fraction having an average molecular weight of about 50,000 to 100,000 exhibits high cell mobilization activity and is, therefore, useful in wound healing applications without exhibiting undesirable inflammatory reactions. The HYALECTIN fraction, having an average molecular weight of about 500,000 to 730,000, has been shown to be useful for ocular and intraarticular injection due to its high molecular weight and inherent viscosity, and, at the same time, does not stimulate cell mobilization activity or inflammatory reactions which are undesirable side effects to be avoided in these pharmaceutical applications.

More specifically, the HYALASTINE fraction has been found to be useful as a wound healing preparation because of the following characteristics.

1. The preparation promotes a remarkably shortened healing time, as compared to conventional therapy, with rapid clearing of the affected area, regularization of ulcer edges, vigorous development of granulation tissue, activation of cellular migration of macrophages and fibroblasts and early epithelization.
2. The preparation promotes increased amenability to reconstructive surgery in the more severe cases.
3. The absence of keloid or retracting scar formation, with final reshaping of cicatricial tissue yielding good cosmetic and functional results.

The HYALASTINE preparation has been found to be useful for the treatment of various wounds including decubitus sores (bed sores), trophic ulcers, burns, indolent wounds, post-traumatic ulcers, varicose and postphlebitic ulcers from venous blood stains, radionecroses, skin lesions, skin grafts and skin lesions due to herpes simplex. For these wound healing treatments, the HYALASTINE preparation, or the sodium salt thereof, can be administered in various methods, such as by gauze pads, cream, spray or ampoules for intradermal injection. For the topical applications as a cream or on a gauze pad, the HYALASTINE is preferably combined with an emulsifying agent, which absorbs the exudate from the exposed area while affording excellent diffusion of hyaluronic acid, and a water-dispersible excipient so that the wound dressing is easily removed.

The HYALECTIN fraction has been found to be particularly useful for the treatment of horses, particularly race horses, suffering from joint disorders and diseases caused by acute or chronic trauma, infections or repeated intraarticular corticosteroid injections. Specific examples of disorders treatable with HYALECTIN are osteoarthrosis with or without inflammatory signs, acute or chronic synoritis, degenerative processes in articular cartilage, and dry joint disease. The most frequent symptoms of these disorders are generally pain, impaired joint function, and reduced joint flexion. The HYALECTIN fraction of the invention has been found to promote marked reduction of the healing time for such affected horses as compared with conventional therapy, to promote early and lasting improvement of joint function and to reduce pain and lameness. These clinically advantageous effects are believed to be promoted by a normalization of the viscoelasticity of the synovial fluid and by activation of tissue repair processes in the articular cartilages.

Moreover, all the above advantageous effects are promoted by the HYALECTIN fraction in the absence of local and/or systemic toxic effects. Repeated administration of HYALECTIN produces no evidence of allergic reactions nor any adverse or lasting effects.

PHARMACEUTICAL PREPARATIONS

The above disclosure has shown that the HYALASTINE and HYALECTIN fractions have good activity for pharmaceutical applications. The following examples are presented for exemplary purposes only to describe possible pharmaceutical preparations for actual in vivo administration of the HA fractions.

A. Preparations for Wound Healing

| Example 1: | ampoules for intradermal injection-<br>each ampoule contains: | | |
|---|---|---|---|
| | Hyalastine sodium salt | | mg 4 |
| | Sodium Chloride | | mg 16 |
| | Water for injection | q.s.a. | ml 2 |
| Example 2: | ampoules for intradermal injection-<br>each ampoule contains: | | |
| | Hyalastine potassium salt | | mg 5 |
| | Sodium Chloride | | mg 8 |
| | Water for injection | q.s.a. | ml 1 |
| Example 3: | spray-bottle for topical application-<br>each bottle contains: | | |
| | Hyalastine sodium salt | | mg 20 |
| | Sodium Chloride | | mg 80 |
| | Water for injection | q.s.a. | ml 10 |
| Example 4: | spray-bottle for topical application-<br>each bottle contains: | | |
| | Hyalastine potassium salt | | mg 30 |
| | Mannitol | | mg 100 |
| | Water for injection | q.s.a. | ml 10 |
| Example 5: | cream for topical application-<br>each tube of cream contains: | | |
| | Hyalastine potassium salt | | mg 25 |
| | Polyethyleneglycol mono-<br>stearate 400 | | mg 1000 |
| | Cetiol (decyl ester of<br>oleic acid) | | mg 500 |
| | Lanette SX (cetyl-stearyl<br>alcohol + lauryl sulfate 9:1) | | mg 150 |
| | Glycerol | | mg 200 |
| | Sorbitol | | mg 150 |
| | Na-dehydroacetate | | mg 10 |
| | p-oxymethylbenzoate | | mg 7.5 |
| | p-oxypropylbenzoate | | mg 5 |
| | redistilled water | q.s.a. | g 10 |
| Example 6: | cream for topical application-<br>each tube of cream contains: | | |
| | Hyalastine sodium salt | | mg 30 |
| | Paraffin jelly | | mg 3 |
| | Polyethyleneglycol mono-<br>stearate 400 | | mg 1000 |
| | Cetiol (decyl ester of oleic<br>acid) | | mg 500 |
| | Lanette SX (cetyl-stearyl<br>alcohol + lauryl sulfate 9:1) | | mg 150 |
| | Glycerol | | mg 200 |
| | Sorbitol | | mg 150 |
| | Na-dehydroacetate | | mg 10 |
| | p-oxymethylbenzoate | | mg 7.5 |
| | p-oxypropylbenzoate | | mg 5 |
| | redistilled water | q.s.a. | g 10 |
| Example 7: | medicated gauze pads for topical<br>application-<br>each gauze-pad measuring<br>10 × 10 cm contains: | | |
| | Hyalastine sodium salt | | mg 3 |
| | Glycerol | | g 1 |
| | Polyethyleneglycol | | g 2 |
| | redistilled water | q.s.a. | g 3 |
| Example 8: | medicated gauze-pads for topical<br>application-<br>each gauze-pad measuring<br>15 × 15 cm contains: | | |
| | Hyalastine potassium salt | | mg 6 |
| | Paraffin jelly | | mg 0.5 |
| | Glycerol | | g 1 |
| | Polyethyleneglycol | | g 2 |
| | redistilled water | q.s.a. | g 3 |
| Example 9: | dry powder for wound healing<br>application-each gram of dry<br>powder contains: | | |
| | Hyalastine sodium salt | | mg 10 |
| | Mannitol | | g 0.75 |
| | Glycine | | g 0.24 |

B. Preparations for Intraocular Use

| Example 10: | 1-ml vials-<br>each vial contains: | | |
|---|---|---|---|
| | Hyalectin sodium salt | | mg 10 |
| | Sodium Chloride | | mg 8 |
| | Monobasic sodium phosphate<br>$2H_2O$ | | mg 0.25 |
| | Dibasic sodium phosphate<br>$12H_2O$ | | mg 3 |
| | Water for injection | q.s.a. | ml 1 |
| Example 11: | 5-ml vials-<br>each vial contains: | | |
| | Hyalectin potassium salt | | mg 60 |
| | Mannitol | | mg 50 |
| | Monobasic sodium phosphate<br>$2H_2O$ | | mg 1.25 |
| | Dibasic sodium phosphate<br>$12H_2O$ | | mg 15 |
| | Water for injection | q.s.a. | ml 5 |
| Example 12: | preloaded syringes-<br>each syringe contains: | | |
| | Hyalectin sodium salt | | mg 40 |
| | Sodium Chloride | | mg 16 |
| | Monobasic sodium phosphate<br>$2H_2O$ | | mg 0.8 |
| | Dibasic sodium phosphate<br>$12H_2O$ | | mg 8.16 |
| | Water for injection | q.s.a. | ml 2 |

C. Preparations for Intra-Articular Use

| Example 13: | 2-ml vials-<br>each vial contains: | | |
|---|---|---|---|
| | Hyalectin sodium salt | | mg 40 |
| | Sodium Chloride | | mg 16 |
| | Water for injection | q.s.a. | ml 2 |
| Example 14: | 4-ml vials-<br>each vial contains: | | |
| | Hyalectin potassium salt | | mg 60 |
| | Mannitol | | mg 35 |
| | Glycine | | mg 10 |
| | Water for Injection | q.s.a. | ml 4 |
| Example 15: | preloaded syringes-<br>each syringe contains: | | |
| | Hyalectin sodium salt | | mg 25 |
| | Sodium Chloride | | mg 12 |
| | Mannitol | | mg 10 |
| | Monobasic sodium phosphate<br>$2H_2O$ | | mg 0.5 |
| | Dibasic sodium phosphate<br>$12H_2O$ | | mg 6 |
| | Water for injection | q.s.a. | ml 2 |

Although the above-preparations have been described for exemplary purposes, it will be appreciated that other pharmaceutical formulations could be prepared by combining the HYALASTINE and HYALECTIN fractions discovered by the inventors, or the potassium or sodium salts thereof, with other pharmaceutically acceptable carriers, diluents, or excipients and at various dosages depending upon the particular use for the formulation.

For wound healing uses, the preparations of the HYALASTINE fraction are applied to the affected skin areas in one of the dosage forms discussed above, that is, either as a cream, a spray, on a gauze-pad, as a dry powder or as an intradermal injection.

For intraarticular uses, the preparations of the HYALECTIN are generally administered at a dosage rate of 2 ml per joint taken either from a prepared vial or a preloaded syringe as described above.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A substantially pure, non-inflammatory hyaluronic acid fraction having an average molecular weight of between 30,000 and 730,000, and which is free of low molecular weight hyaluronic acid having a molecular weight of less than 30,000.

2. A substantially pure, non-inflammatory hyaluronic acid fraction as in claim 1, having an average molecular weight of between about 250,000 and about 350,000.

3. A substantially pure, non-inflammatory hyaluronic acid fraction as in claim 1, having an average molecular weight of about 30,000 to about 100,000.

4. A substantially pure, non-inflammatory hyaluronic acid fraction as in claim 1, having an average molecular weight of between about 50,000 and about 100,000.

5. A substantially pure, non-inflammatory hyaluronic acid fraction as in claim 1, having an average molecular weigh of between about 500,000 and about 730,000.

6. A sodium salt or potassium salt of the hyaluronic acid fraction according to claim 2.

7. A sodium salt or potassium salt of the hyaluronic acid fraction according to claim 3.

8. A sodium salt or potassium salt of the hyaluronic acid fraction according to claim 4.

9. A sodium salt or potassium salt of the hyaluronic acid fraction according to claim 5.

10. A pharmaceutical composition containing an effective wound healing amount of the hyaluronic acid fraction according to claim 2, and at least one pharmaceutically acceptable carrier, excipient, or diluent.

11. A pharmaceutical composition containing an effective wound healing amount of a hyaluronic acid fraction according to claim 3, and at least one pharmaceutically acceptable carrier, diluent, or excipient.

12. A pharmaceutical composition containing an effective intraocular or intraarticular treatment amount of a hyaluronic acid fraction according to claim 4, and at least one pharmaceutically acceptable carrier, excipient, or diluent.

13. A pharmaceutical composition containing an effective intraocular or intraarticular treatment amount of a hyaluronic acid fraction according to claim 5, and at least one pharmaceutically acceptable carrier, excipient, or diluent.

14. A method for enhancing the healing of tissue wounds comprising administering to a host in need thereof an effective wound healing amount of a hyaluronic acid fraction according to claim 2.

15. A method for enhancing the healing of tissue wounds comprising administering to a host in need thereof an effective wound healing amount of a hyaluronic acid fraction according to claim 3.

16. A method for enhancing the healing of tissue wounds comprising administering to a host in need thereof an effective wound healing amount of a hyaluronic acid fraction according to claim 4.

17. A method for treating traumatic and degenerative diseases of the joints, and for improving joint function, comprising injecting into an affected joint of a host in need thereof, an effective amount of a hyaluronic acid fraction according to claim 5.

18. A method for intraocular treatment comprising injecting into the ocular area of a host in need thereof, a hyaluronic acid fraction according to claim 5 to substitute for endobulbar liquids.

19. A substantially pure, non-inflammatory hyaluronic acid fraction having an average molecular weight of between 50,000 and 350,000, and which is free of low molecular weight hyaluronic acid having a molecular weight of less than 30,000.

20. A sodium or potassium salt of the hyaluronic acid fraction according to claim 19.

21. A pharmaceutical composition containing an effective wound healing amount of a hyaluronic acid fraction according to claims 19 or 20, and at least one pharmaceutically acceptable carrier, diluent or excipient.

22. A method for enhancing the healing of tissue wounds which comprises administering an effective wound healing amount of a hyaluronic acid fraction according to claims 19 or 20.

* * * * *

UNITED STATES PATENT AND TRADEMARK OFFICE
CERTIFICATE OF CORRECTION

PATENT NO. : 5,925,626
DATED : July 20, 1999
INVENTOR(S) : della Valle et al.

It is certified that error appears in the above-identified patent and that said Letters Patent is hereby corrected as shown below:

Title page item "[63] Related U.S. Application Data", please change

"Dec. 23, 1984" to -- Dec. 23, 1983 --.

Signed and Sealed this

Twenty-eighth Day of March, 2000

Attest:

Q. TODD DICKINSON

*Attesting Officer*  *Commissioner of Patents and Trademarks*